United States Patent [19]

Arnberg

[11] Patent Number: 4,781,058

[45] Date of Patent: * Nov. 1, 1988

[54] METHOD AND APPARATUS FOR MEASURING LOAD BEARING CAPACITY OF TRAFFIC-CARRYING SURFACES

[75] Inventor: Peter W. Arnberg, Odeng 75, 11322 Stockholm, Sweden

[73] Assignees: Peter W. Arnberg; Sten Engwall, both of Solna; Sture Tordhag, Vallingby, all of Sweden; a part interest

[*] Notice: The portion of the term of this patent subsequent to Apr. 21, 2004 has been disclaimed.

[21] Appl. No.: 6,700

[22] Filed: Jan. 22, 1987

Related U.S. Application Data

[63] Continuation of Ser. No. 776,502, Sep. 16, 1985, Pat. No. 4,658,639.

[30] Foreign Application Priority Data

Sep. 17, 1984 [SE] Sweden .................... 8404663

[51] Int. Cl.$^4$ .................... G01N 3/40; G01B 11/00
[52] U.S. Cl. .................... 73/84; 73/146; 356/376; 364/550
[58] Field of Search .................... 73/84, 146, 105; 364/506, 550, 556; 356/376

[56] References Cited

U.S. PATENT DOCUMENTS

| | | |
|---|---|---|
| 2,280,592 | 4/1942 | LeMieux, Jr. |
| 3,383,913 | 5/1968 | Swift .................... 73/146 |
| 3,444,727 | 5/1969 | Bourdin et al. .................... 73/78 |
| 3,483,744 | 12/1969 | Goldberg .................... 73/146 |
| 4,348,901 | 9/1982 | Vural et al. .................... 73/594 |
| 4,393,691 | 7/1983 | Koehne .................... 73/84 |
| 4,400,970 | 8/1983 | Ali .................... 73/9 |
| 4,571,695 | 2/1986 | Elton et al. .................... 364/550 |
| 4,645,917 | 2/1987 | Penney et al. .................... 364/556 X |
| 4,653,316 | 3/1987 | Fukuhara .................... 73/146 |
| 4,658,639 | 4/1987 | Arnberg .................... 73/84 |
| 4,685,806 | 8/1987 | Arnberg .................... 73/146 X |

FOREIGN PATENT DOCUMENTS

59-17106 1/1984 Japan .
59-27247 2/1984 Japan .
1024545 6/1983 U.S.S.R. .................... 73/146

OTHER PUBLICATIONS

Lampinen, Variation av barigheten i vagens tavarprofil, ("Variation of the Carrying Capacity in Transverse Profile of the Road"), State Technical Research Center, Research Report No. 122, Esbo (1983).
Reinslett, Vegers Baereevne, ("Carrying Capacity of Roads"), Directorate of Roads, Road Laboratory, Oslo, Norway (1982).
Nielsen, Sammenlignende baereevnemalinger med forskelligt inventering sudstyr, ("Caparative Carrying Capacity With Various Data Gathering Equipment"), State Highways Laboratory Report No. 124, Roskilde (Jul. 1981).

Primary Examiner—Tom Noland
Attorney, Agent, or Firm—Willian Brinks Olds Hofer Gilson & Lione Ltd.

[57] ABSTRACT

A method and apparatus are provided for measuring the load bearing capacity of a surface by continuously transporting a known load along the surface and measuring the resulting deformation thereof. In one embodiment a contactless laser transducer is mounted directly in front of and behind a loaded wheel for measuring the elevation of the surface before and after the load. A computer determines the difference between the measured elevations which is indicative of the load bearing capacity of the surface. Conventional recording, display, and storage equipment are provided for recording, displaying, and storing the elevation values and the corresponding differences. The load velocity and longitudinal position may also be determined and stored with the corresponding elevation and difference values. In another embodiment, the contactless laser transducers directly in front of and behind the loaded wheel are replaced with racks of laser transducers which also extend laterally of said wheel to produce transverse elevational surface profiles in place of individual elevation points directly in front of and behind the wheel.

16 Claims, 3 Drawing Sheets

METHOD AND APPARATUS FOR MEASURING LOAD BEARING CAPACITY OF TRAFFIC-CARRYING SURFACES

This application is a continuation of application Ser. No. 776,502 filed Sept. 16, 1985, now U.S. Pat. No. 4,658,639.

BACKGROUND OF THE INVENTION

The invention disclosed herein relates to a process and apparatus for measuring the load bearing capacity of traffic-carrying surfaces such as roadways, runways, piers, terminals, and the like.

The need to measure the load bearing capacity of traffic-carrying surfaces arises in a variety of contexts. For example, there is a need to determine the load bearing capacity of newly constructed surfaces to determine whether the meet stated specifications. In addition, it is useful to be able to measure the load bearing capacity of a surface to determine whether reinforcement is required, as well as the extent to which the surface might be damaged when deciding whether to allow an especially heavy load to be transported over the surface. Also, the load bearing capacity of certain surfaces change with the weather and the seasons so that it is useful to be able to determine and post the maximum load capacity of the surface at various times and under various conditions. The expected life of a particular traffic carrying surface can also be estimated based on the maximum loads to be allowed thereon and the estimated frequency with which the surface will be subjected to such loads. It is also of interest to be able to quickly, accurately, and inexpensively discover weaknesses in a traffic carrying surface at an early stage so that they can be repaired promptly, and major construction, with attendant higher costs, can be avoided.

It is known that an estimate of the load bearing capacity of a surface can be obtained by examining the deformation of the surface when a known load is applied. The form and degree of the resulting depression or deformation are influenced by inhomogeneities in the surface material, vertical and lateral variations in the packing of the underlying layers, moisture conditions, proximity to the surface edge, and other factors which effect the maximum safe load bearing capacity. Generally, the maximum safe load bearing capacity varies inversely with the degree of surface deformation observed. Using modern mechanical measuring instruments, which can accurately measure surface deformation in the order of 0.1–0.2 millimeters, it has been found, for example, that even the very best roadways will exhibit deformation in the range of 0.1 millimeters near the point where the load contacts the surface. It is also known that the load bearing capacity of a particular surface is evidenced not only by the longitudinal deformation of the surface when under load but also by the lateral deformation thereof. For example, whereas a longitudinal "funnel" deformation is indicative of deep underlying damage, a broad, shallow, transverse deformation indicates shallower superficial damage.

A proliferation of new highways, airports, shipping terminals, and the like, and a marked increase in the volume and weight of the traffic using these facilities have been observed over the past several decades. As a result, the ability to quickly, accurately, and efficiently measure the load bearing capacities of such surfaces with minimal interference in each of the contexts previously mentioned has become of significant importance. Previously, a number of attempts have been made, based on the measurement of surface deformation with a known load, to satisfy the need. However, for a variety of reasons, each of these attempts has produced less than satisfactory results.

One approach includes dropping on angularly shaped pointed weight onto the surface being tested and determining the load bearing capacity from the resulting deformation of the road surface. This approach has been found unsatisfactory in that it is time consuming and requires the interruption of traffic flow on the portion of surface being tested.

Another approach employs a slowly or intermittently advancing vehicle to carry a "stamping" device which periodically "stamps" the surface, after which the deformation thereof is measured. Again, this approach is time consuming, and in addition creates a traffic hazard due to the slow speed of the testing vehicle.

Still another approach involves exposing the surface being tested to vibrations on a load from a stationary testing vehicle, and then measuring the depth and shape of the resulting depression. This approach likewise is time consuming. In addition, it can cause a certain amount of damage to the surface and is expensive.

An additional problem common to approaches wherein surface deformation is measured in response to the application of a stationary or slowly moving load is that the measured deformation does not accurately reflect the true load bearing capacity of the surface at the load velocities to which it is likely to be subjected. Such approaches generally underestimate the true load bearing capacity of a surface because a stationary or slowly moving load produces a greater and longer lasting deformation of the surface than does the same load travelling at normal highway velocity, for example.

An overview of these and other prior art approaches to measuring the load bearing capacity of traffic-carrying surfaces is contained in the following documents: Nielsen, *Sammenliguende Beareernemalinger med Forskelligt Inventeringsudestyr* ("*Comparative Carrying Capacity With Various Data Gathering Equipment*"), State Highways Laboratory, Report No. 124, Roskilde (July 1981); Reinslett, *Carrying Capacity of Roads,* Directorate of Roads, Road Laboratory, Oslo, Norway (1982); and Lampinen, *Variation of the Carrying Capacity in Transverse Profile of the Road,* State Technical Research Center, Research Report No. 122, Esbo (1983).

In contrast to previous approaches, measuring the load bearing capacity of traffic-carrying surfaces according to the present invention has the objects and advantages of not causing damage to the surfaces, not interfering with the normal flow of traffic, generating a large number and density of measurements faster and more efficiently than previous approaches, and producing results that much more accurately reflect the true load bearing capacity of the surfaces measured. Further, one presently preferred embodiment of the present invention has the additional objects and advantages of measuring transverse elevational profiles to provide measuring-vehicle-independent surface depression values, and of obtaining data concerning lateral surface deformation to increase the accuracy of the determination of the load bearing capacity of surfaces.

SUMMARY OF THE INVENTION

The above-related objects and advantages of the present invention are achieved by providing a method and apparatus for measuring the load bearing capacity of traffic-carrying surfaces in which a load is transported continuously along the surface to be measured. As the load proceeds, the elevation of the surface in front of the load is measured with respect to a reference elevation. Likewise, the elevation of the surface behind the load is measured with respect to a reference elevation. The difference between the measured elevation of the surface in front of and behind the load is then computed as a measure of the load bearing capacity of the surface.

According to another aspect of the present invention, a method and apparatus are provided for transporting a load continuously along a surface to be measured. As the load proceeds, the transverse profile of the surface is measured at a selected number of points directly in front of and laterally of the load with respect to a reference elevation. The transverse profile of the surface is likewise measured at an equal number of corresponding points directly behind and laterally of the load with respect to a reference elevation. The difference between the two transverse profiles is determined as a measure of the load bearing capacity of the surface.

BRIEF DESCRIPTION OF THE DRAWINGS

An exemplary illustration of a presently preferred embodiment of the present invention is contained in the appended figures in which.

DETAILED DESCRIPTION OF A PRESENTLY PREFERRED EMBODIMENT

The novel features believed to be characteristic of the present invention are set out in the appended claims. The invention itself can be best understood by reference to the following detailed description taken in conjunction with the figures.

Figure 1:
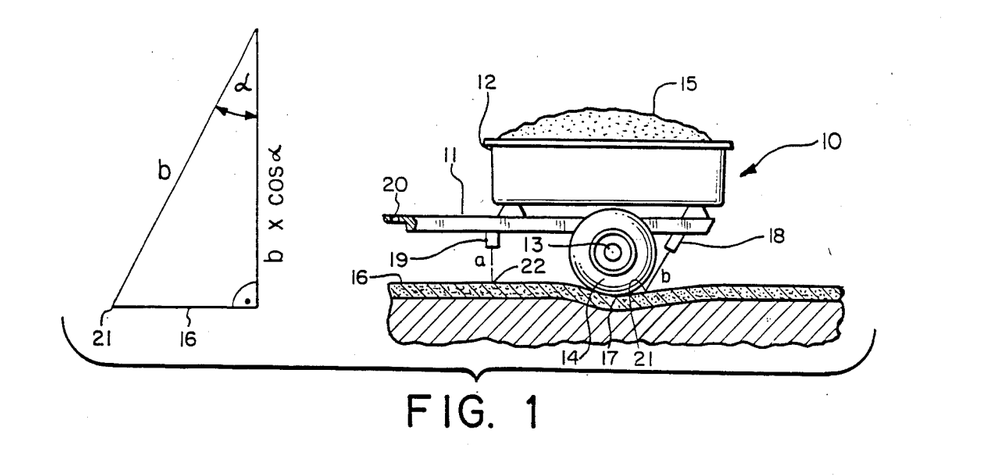
FIG. 1 is a schematic diagram of a rolling load equipped with contactless distance measuring transducers for measuring the elevation of a surface according to one presently preferred embodiment of the invention.

In one presently preferred embodiment of the present invention illustrated in FIG. 1, a surface 16 is subjected to a known load in the form of a weighted trailer 10. The trailer 10 comprises a frame 11 supporting a box 12 loaded with a material 15 of known weight. The frame 11 has a hitch 20 for attachment to a pulling vehicle (not shown). The frame 11 is mounted in conventional fashion to an axle 13 which in turn is supported by one or more wheels 14. The wheels 14 bring the load into rolling contact with the surface 16 at one or more contact points 17. Of course, the locations of the contact points 17 vary continuously as the pulling vehicle pulls the loaded trailer 10 along the surface 16. In order to more accurately simulate actual conditions, and to obtain a more accurate determination of the load bearing capacity of the surface 16 being tested, it is preferred that the weight of the material 15 be within the range of weights to which the surface 16 can be expected to be subjected. Likewise, it is preferable to employ wheels 14 similar to those with which the surface 16 is expected to come into contact. Thus, for example, when testing an airport runway, airplane wheels carrying a load approximately equal in weight to a fully loaded Boeing 747 would preferably be used. In contrast, when measuring a highway, the use of standard truck tires carrying a weight in the same range as trucks actually using the highway is appropriate.

In this preferred embodiment of the present invention, a first contactless distance measuring transducer 19 is mounted on the frame 11 directly in front of one or more of the wheels 14. A second contactless distance measuring transducer 18 is mounted on the frame 11 in line with the first transducer 19 directly behind one or more of the wheels 14. Laser cameras of the type commonly used by those skilled in the art to make such distance measurements are preferred as distance measuring transducers both because of the high rate at which they can sample the surface 16 and because of the accuracy of the samples they produce. In a presently preferred embodiment of the present invention, for example, it has been found that pulsing the laser cameras to provide a sampling rate in the range of 36 kilohertz produces distance samples accurate to approximately 0.1–0.2 millimeters. Other less preferred alternatives include ultrasound and Doppler radar transducers, for example. It is known that the surface deformation produced by a loaded rolling wheel is often funnel-shaped with part of the deformation preceding the wheel. In practice it has been found that this deformation can precede the wheel 14 by a meter or more. The first contactless distance measuring transducer 19 is therefore preferably mounted sufficiently spaced from the wheel 14 to avoid measuring the elevation of the surface 16 in the depressed area preceding the wheel 14.

It has been found that the point of maximum depression of the surface 16 behind the wheel 14 generally occurs approximately one decimeter behind the contact point 17. It is therefore preferable to choose a point of measurement 21 behind the wheel 14 as close as possible to that optimum location in order to obtain the best possible indicia of load bearing capacity. However, it has been found in practice that as the velocity of the load increases, the distance between the contact point 17 and the point of measurement 21 can also be increased somewhat. A problem with measuring the elevation of the surface 16 approximately one decimeter behind the contact point 17 is that the wheel 14 and axle of the trailer 10 tend to obstruct mounting of the second contactless distance measuring transducer 18 directly behind the contact point 17 and directly above the measuring point 21. To avoid this problem, it is preferable to mount the second contactless distance transducer 18 at a distance behind the wheel 14 and, as shown in FIG. 1, to direct it at a forward angle $\alpha$ to establish a line of measurement b to the measuring point 21 on the surface 16 directly behind the point of contact 17. In this arrangement, the second contactless distance measuring transducer 18 generates a distance signal of greater magnitude than if it were mounted directly above the measuring point 21. However, this is easily compensated, as illustrated in FIG. 1, by multiplying the resulting elevation signal by the cosine of the angle $\alpha$. Since $\alpha$ is a constant, its cosine is also a constant and the perpendicular elevation value behind the wheel is defined simply as 37 b cos $\alpha$". In practice it has been found suitable to mount the second contactless distance measuring transducer 18 about a decimeter behind the measuring point 21 with a forward angle of 10–30 degrees from vertical.

Figure 1A:
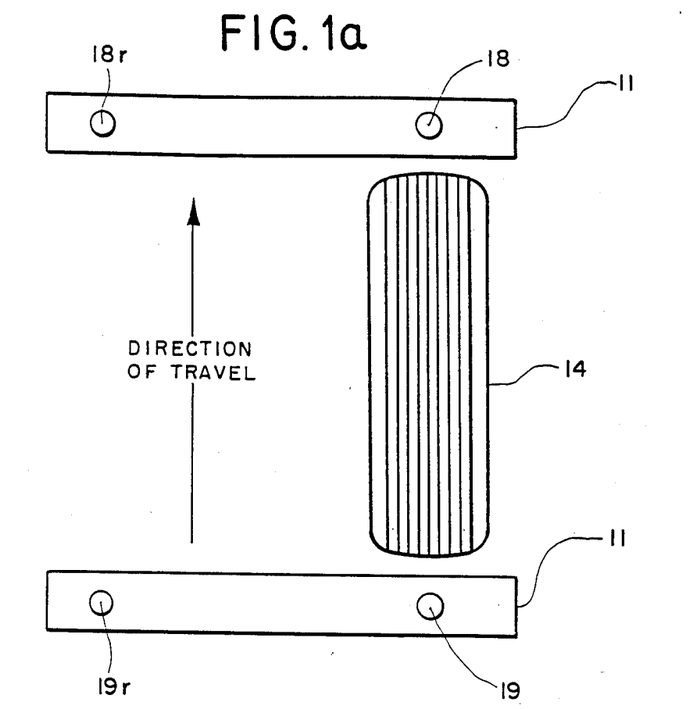
FIG. 1a is a top view of an arrangement of contactless transducers for measuring surface and reference elevations according to one preferred embodiment of the invention.

Referring to FIG. 1a, in addition to the first and second contactless distance measuring transducers 18, 19, one or more contactless reference transducers 18r, 19r are also mounted on the frame 11 of trailer 10. The contactless reference transducers 18r, 19r are preferably also laser camera transducers similar to the first and second distance measuring transducers 18, 19. Preferably also, the first and second contactless reference transducers 18r, 19r are mounted on the frame 11 laterally spaced from the wheels 14 with the first reference transducer 19r being in front of the load and the second reference transducer 18r being behind the load in line with the first reference transducer.

Figure 2:
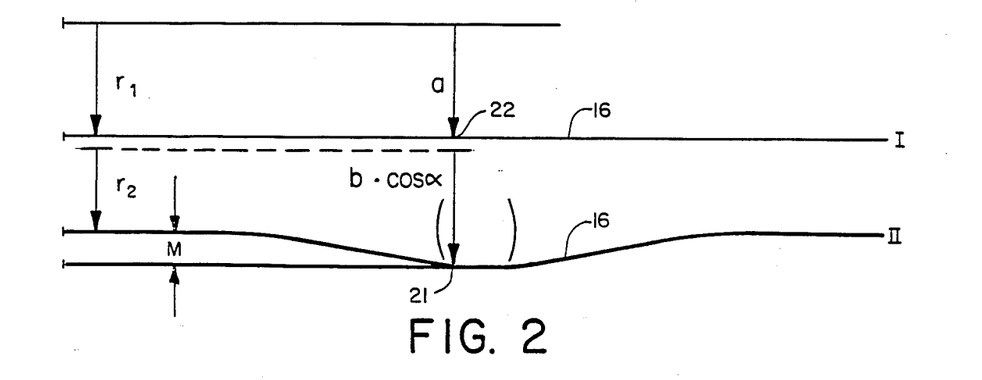
FIG. 2 is a diagrammatic representation of the measured elevation of the surface in front of and behind the load of FIG. 1.

With this arrangement, the depth of the depression in the surface 16 caused by the rolling loaded wheel 14 is determined is illustrated in FIG. 2. In front of the wheel 14, the surface 16 is not deformed. The first contactless reference transducer 19r measures a first reference elevation $r_1$, and the first contactless distance measuring transducer 19 measures an elevation a. Behind the wheel 14, the second contactless reference transducer-measures a second reference elevation $r_2$ and the second contactless distance measuring transducer 18 generates a compensated elevation value "b cos $\alpha$" as described above. The total depression M of the surface 16 is expressed by the equation:

$$M = (b \cos \alpha - r_2) - (a - r_1)$$

It is, of course, possible to use a single reference transducer in front of the load or elsewhere instead of one in front and one behind. In that case, since both elevation values are measured with respect to the same reference, they may be subtracted directly. The above equation then becomes:

$$M = b \cos \alpha - a$$

However, the first arrangement and formulation are preferred because they better account for unloaded surface irregularities commonly encountered in actual surfaces in practice.

It should be apparent to those skilled in the art that if both the first and second contactless distance measuring transducers 18, 19 sample the surface 16 simultaneously, they will measure the elevation of the same point on the surface 16 in a longitudinal direction before and after contact with the loaded wheel 14 only if the velocity of the trailer 10 is maintained perfectly constant. It should also be apparent that this is impracticable since at sampling rates in the tens of kilohertz even very slight velocity deviations result in different points being sampled, thus introducing inaccuracies into the computed depression value M.

Figure 5:
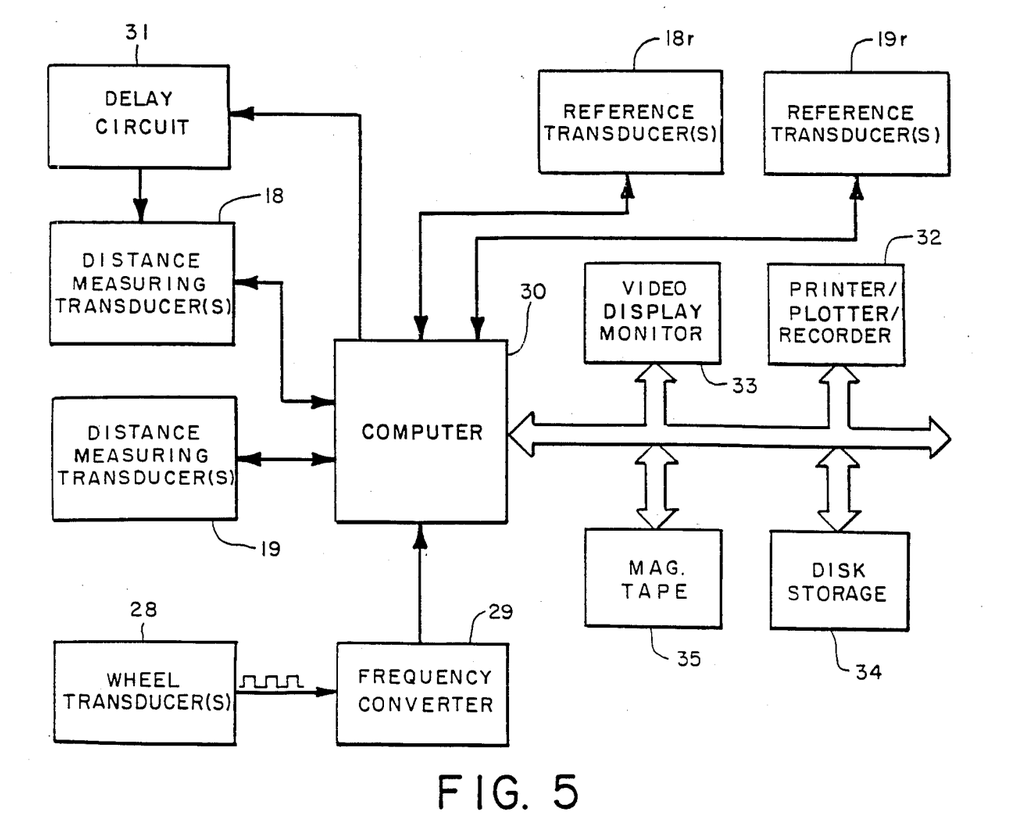
FIG. 5 is a block diagram illustrating the interconnections of the transducer, processing, and recording elements of the presently preferred embodiment of the invention.

To overcome this problem, it is preferred to determine the velocity of the trailer 10 each time the first contactless distance transducer 19 samples the surface 16 and to delay sampling by the second contactless distance transducer 18 as a function of the measured velocity so that it samples the same point longitudinally on the surface 16 as the first contactless distance measuring transducer 19. With reference to FIG. 5, the velocity trailer 10 is obtained preferably from a conventional electro-optical wheel transducer. The wheel transducer 28 produces pulses at unit distances as the wheel 14 of the trailer 10 turns, or alternatively as a wheel of a pulling vehicle turns. The frequency of the pulses is related to the velocity of the load. A signal representative of the velocity is preferably obtained by inputting the pulse train into a conventional frequency converter 29. The converter output signal in turn is used by a computer for example to program a conventional delay circuit 31. The amount of delay is calculated from the velocity and the fixed longitudinal distance between the first and second contactless distance transducers 18, 19. For example, if the distance of separation is two (2) meters, and the velocity $v_o$ and time $t_o$ when the first contactless distance measuring transducer 19 sampled the surface 16 are known, then the time $t_1$ when the second contactless distance measuring transducer 18 should sample the same point on the surface 16 is expressed as:

$$t_1 = t_o + 2/v_o$$

Knowing the appropriate delay time ($2/v_o$), the conventional delay circuit 31 is programmed to delay sampling by the second contactless distance measuring transducer 18 for the appropriate time.

The longitudinal position of the load is also preferably determined each time the surface is sampled by the first contactless distance measuring transducer 19. The longitudinal position is preferably obtained from the electro-optical wheel transducer 28 by counting the number of unit distance pulses produced thereby.

A conventional computer 30 of the type commonly used by those skilled in the art in many data acquisition and processing applications receives the signals generated by the reference transducers, by the first and second contactless distance measuring transducers 18, 19, and by the electro-optical wheel transducer 28 and frequency converter 29. It is preferable for reasons of both cost and space conservation for the computer to be a "board" computer. The computer processes the received signals according to the equations described above. In addition it interfaces with conventional hardcopy recording and/or display equipment and off-line storage such as chart recorders 32, video monitors 33, and magnetic disk 34 or tape 35 drives to display, record, and store the various corresponding reference, elevation, depression, distance, and velocity values for later analysis and processing.

In a second presently preferred embodiment of the present invention, the first and second contactless distance measuring transducers 18, 19 are replaced by a first and second rack of such transducers. In this preferred embodiment, a transverse elevational profile of the surface 16 is measured before and after the load instead of individual elevations directly in front of and behind the wheels 14.

Figure 4:
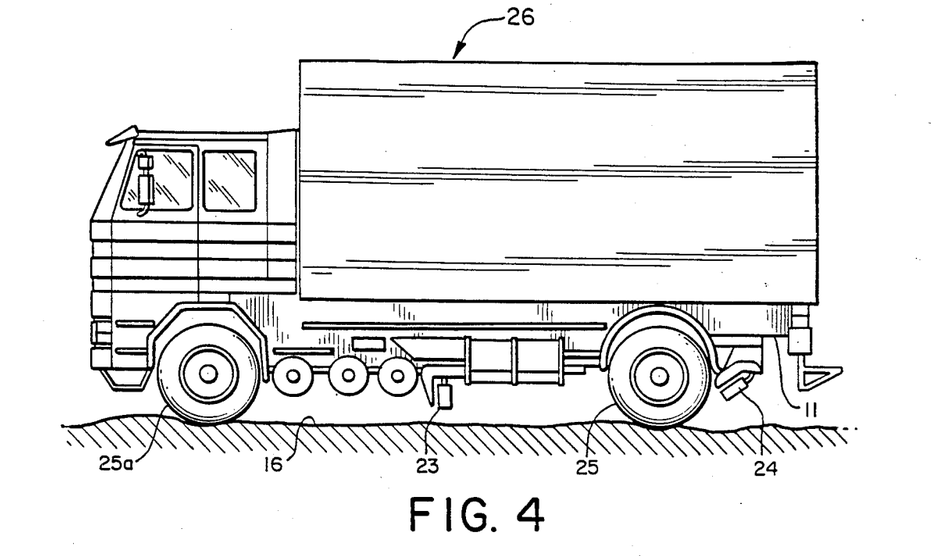
FIG. 4 is a diagram of a rolling load having two axles and equipped with two racks of contactless distance measuring transducers embodiment of the invention.
Figure 4A:
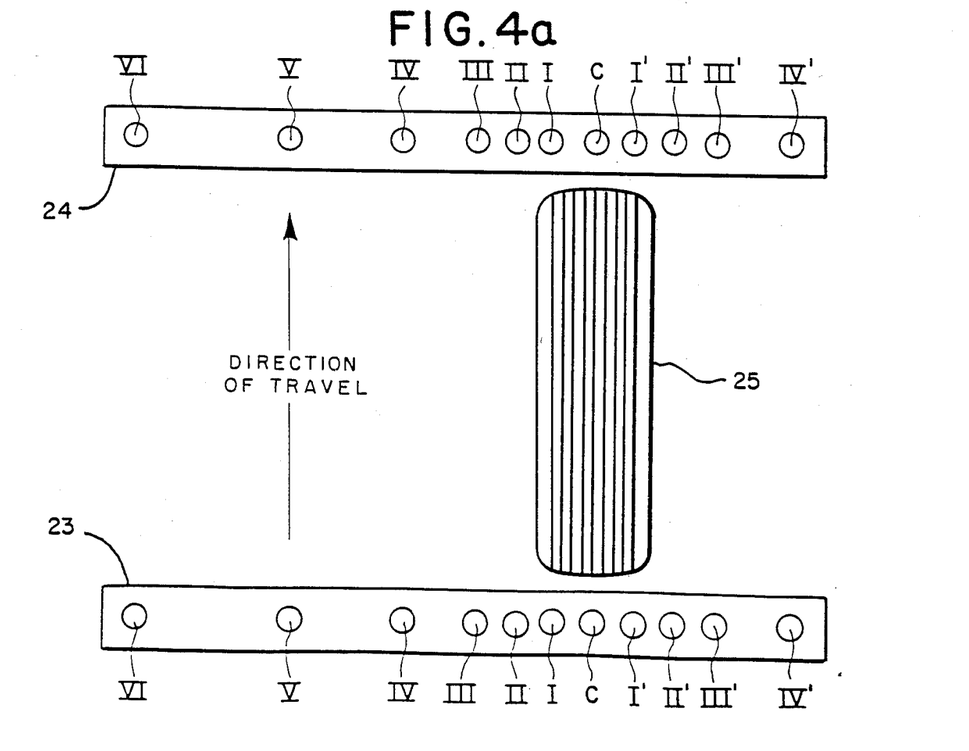
FIG. 4a is a top view of the racks of contactless transducers of FIG. 4.

As illustrated in FIGS. 4 and 4a, the trailer 10 can be replaced by a road vehicle 26 having a lightly loaded front axle and a heavily loaded rear axle. The first rack of transducers 23 is mounted to the frame 11 of the vehicle in front of the rear wheels 25 transversely to the direction of motion of the frame 11. The second rack of transducers 24 is mounted to the frame 11 behind the rear wheels 25 parallel and in line with the first rack 23. The spacing of the first and second racks in front of and behind the rear wheels 25 and the angular orientation of the distance transducers behind the rear wheels 25 correspond to the spacing and orientation described above with respect to the other presently preferred embodiment of the invention and illustrated in FIG. 1. The sampling delay between the transducers on the first and second racks 23, 24 is also as previously described.

Figure 3:
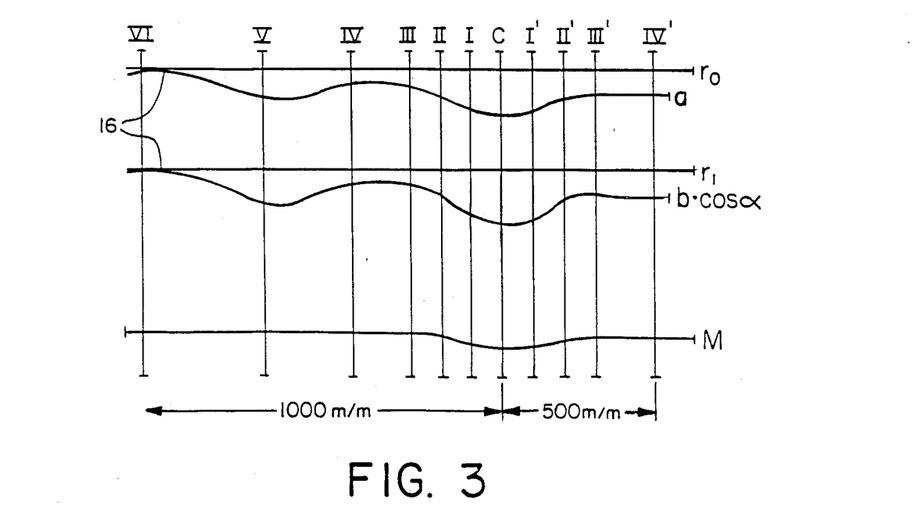
FIG. 3 is a diagrammatic representation of transverse road profiles measured in front of and behind the load of FIG. 1, and of the algebraic difference between the profiles, all measured according to a second presently preferred embodiment of the invention.

As illustrated in FIGS. 3 and 4a, the first and second racks 23, 24 each contain eleven (11) contactless distance measuring transducers mounted in identical positions. A first pair of such transducers denoted by the letter "C" is mounted directly in front of and behind a rear wheel 25. On one side of pair C are mounted transducer pairs I, II, III, and on the other transducer pairs I', II', III'. The lateral spacing on each rack between each element of transducer pairs I, II, III, and C is 50 millimeters. The same is true of the lateral spacing on each rack between the elements of transducer pairs I', II', III', and C. At a lateral distance of 500 millimeters from transducer pair C on either side thereof are mounted transducer pairs IV and IV'. The transducer pair V is mounted 700 millimeters to the left of transducer pair C, and the transducer pair VI is mounted one (1) meter to the left of the transducer pair C. Of course, this transducer arrangement or variations thereof may, if desired, be duplicated for each loaded wheel. It is preferred that the transducer pairs spaced furthest laterally from the loaded rear wheels 25 be used to establish reference elevations for the remaining transducer pairs. Thus, in this embodiment it is preferred that transducer pairs VI and IV' establish reference elevations in front of and behind the load for transducer pairs I-V and I'-III'. It is also preferred that the vertical height of the outside transducer pairs VI and IV' be adjustable so that the transducers of pair VI initially measure the same reference elevation in front of and behind the load and the transducers of pair IV' likewise measure the same reference elevation in front of and behind the load.

As further illustrated in FIG. 3 a transverse profile "a" consisting of the elevation values measured by the distance transducers in front of the loaded rear wheels 25 with respect to a straight-line reference elevation $r_o$ is obtained each time the surface 16 is sampled. Likewise, after a suitable delay, a transverse profile "b cos α" consisting of the compensated elevation values measured by the distance transducers behind the loaded rear wheels 25 is produced with respect to a straight-line reference elevation $r_1$. Since each elevation of each profile is measured with respect to a straight line reference elevation $r_o$, $r_1$ mathematically established between the reference elevations measured by the two outside transducer pairs VI and IV', each profile is vehicle independent, e.g., each profile is independent of vehicle inclination due to a damaged frame 11 or due to a shifting load. The depression M of the surface 16 due to the loaded wheels 25 is obtained in a manner similar to that described above with respect to the other preferred embodiment by subtracting profile "a" from profile "b cos α." As with the other preferred embodiment, a conventional computer, data recorder, display, and off-line storage process, record, display, and store the various data previously described.

It has been found that error is introduced into the calculated transverse depression profile M if the first and second racks 23, 24 are not maintained horizontal to the surface 16 while it is being sampled. This can result, for example, from a damaged frame 11 which causes inclination of the road vehicle 26, or from shifting of the load. Likewise, error is introduced into the calculated depression profile M when the road vehicle 26 proceeds through a curve. In a curve, the outer front wheel 25a of the road vehicle 26 travels at a faster rate and over a greater distance than the inner front wheel. As a result, the path travelled by the first rack 23 is necessarily different than the path travelled by the second rack 24, and the contactless distance measuring transducer pairs on the first and second racks 23, 24 do not sample the same points on the surface 16. The points sampled by the contactless distance measuring transducers on the second rack 24 are laterally offset from the points sampled by the contactless distance measuring transducers on the first rack 23. The amount of the lateral offset depends on the sharpness of the turn made by the front wheels of the road vehicle 26.

To compensate for these error producing situations, the vertical and lateral positions of the first and second racks 23, 24 are preferably adjustable via a conventional hydraulic control system, or alternatively, via a motor driven system. To compensate for inclination of the road vehicle 26, for instance, a conventional hydraulic lift can be positioned under each end of a rack. With the aid of an inclinometer, for example, the lifts can be raised or lowered to adjust the position of the rack to compensate for the error producing inclination. The lateral position of a rack can be similarly controlled by hydraulic lift. In this case, it is also preferable to include electro-optical distance transducers on both front wheels 25a of the road vehicle 26, so that the number of distance pulses from each transducer can be compared, and the difference used as a control signal to the hydraulic lift to adjust the lateral position of the rack accordingly as the road vehicle 26 proceeds through a curve.

In both preferred embodiments of the present invention it has been found beneficial to use laser points having diameters of approximately one centimeter to avoid the effects of stones, cracks, and the like on the surface being tested. Also, in both preferred embodiments, it has been found useful to have the computer calculate the mean of the elevational values produced by each reference and each distance transducer over every decimeter or other selected distance to also avoid the effects of stones, cracks, and the like as well as to provide data in a format useful in determining a prognosis of surface condition. Differences in the mean values and standard deviations of successive transverse profiles are especially useful in this regard since, as a general rule, the greater the difference, the worse the load bearing capacity of the surface. Finally, it has been found suitable to perform the measurements described herein with either preferred embodiment at a wide range of highway velocities up to approximately 70 km/hour.

What have been described are exemplary, presently preferred embodiments of the present invention. It is understood that various changes and modifications to the presently preferred embodiments described herein will be apparent to those skilled in the art. Such changes and modifications can be made without departing from the spirit and scope of the present invention. It is, therefore, intended that such changes and modifications be covered by the following claims.

I claim:

1. A method for measuring the load bearing capacity of a traffic-carrying surface, comprising the steps of:
   (a) continuously transporting a load along said surface with at least one contact point between said load and said surface;
   (b) measuring the elevation of the surface at a first plurality of points in front of said at least one contact point in a direction transverse to the direction of travel of the load and producing therefrom a plurality of first measured values;
   (c) measuring the elevation of the surface at a second plurality of points corresponding to said first plurality of points behind said at least one contact point and producing therefrom a plurality of second measured values; and
   d) determining the difference between each of said first plurality of measured values and each of said corresponding second plurality of measured values to generate a plurality of values defining a transverse profile of the surface.

2. The method of claim 1 further comprising the steps of:
   determining the velocity of the load when the elevation of the surface in front of said at least one contact point is measured; and
   delaying the measurement of the elevation of the surface behind said at least one contact point as a function of said velocity so that the elevation of the surface behind said at least one contact point is measured at substantially the same plurality of points where the elevation in front of said at least one contact point was measured.

3. The method of claim 1 further comprising the steps of:
   determining the longitudinal position of the load when the elevation of the surface is measured; and
   storing said longitudinal position with the corresponding plurality of values defining the transverse profile of the surface at that longitudinal position.

4. The method of claim 1 further comprising the steps of:
   determining the velocity of the load when the elevation of the surface is measured; and
   storing said velocity with the corresponding plurality of profile values defining a transverse profile of the surface.

5. The method of claim 1 wherein the steps of measuring the elevation of said surface in front of and behind said at least one contact point include measuring said elevation in measuring pulses.

6. The method of claim 5 wherein each said measuring pulse is of sufficient duration to cover approximately 1–10 centimeters of said surface in the direction of travel of said load.

7. The method of claim 1 further comprising the steps of:
   forming the mean value of successively measured elevations of the surface in front of and behind said at least one contact point over a selected distance; and
   forming the mean value of the differences between successively measured elevations of the surface at corresponding points in front of and behind said at least one contact point over a selected distance.

8. The method of claim 1 wherein the step of measuring the elevation of the surface behind said at least one contact point includes measuring the elevation at a selected angle and compensating the measured value for said angle.

9. An apparatus for measuring the load bearing capacity of a traffic-carrying surface, comprising:
   a load for continuously travelling along said surface;
   means for bringing said load into contact with said surface at least one contact point;
   first measuring means for measuring the elevation of said surface at a first plurality of points in front of said at least one contact point in a direction transverse to the direction of travel of said load;
   second measuring means for measuring the elevation of said surface at a second plurality of points corresponding to said first plurality of points behind said at least one contact point; and
   means for determining the difference between the measured elevation of said surface at each of said first plurality of points and at each of said corresponding second plurality of points to generate a plurality of values defining a transverse profile of said Surface.

10. The apparatus of claim 9 further comprising:
    means for determining the longitudinal position of the load when an elevation measurement is taken; and
    means for storing said longitudinal position with the corresponding plurality of values defining the transverse profile of said surface at that longitudinal position.

11. The apparatus of claim 9 further comprising:
    means for determining the velocity of the load when an elevation measurement is taken; and
    means for storing said velocity with the corresponding plurality of values defining the transverse profile of said surface.

12. The apparatus of claim 9 wherein:
    said first measuring means comprises a first plurality of distance measuring devices positioned transversely to the direction of travel of said load for measuring the elevation of said surface at said first plurality of points in front of and laterally of said at last one contact point; and
    said second measuring means comprises a second plurality of distance measuring devices in positions corresponding to the positions of said first plurality of distance measuring devices for measuring the elevation of said surface at said second plurality of points behind and laterally of said at least one contact point.

13. The apparatus of claim 9 further comprising means for determining the velocity of said load, and means for delaying the measurement of said elevation by said second measuring means relative to said first measuring means as a function of said velocity so that said first and second measuring means measure substantially the same points of said surface.

14. The apparatus of claim 9 wherein said first and second measuring means comprise means for measuring said elevation of said surface in measuring pulses.

15. The apparatus of claim 9 wherein said second measuring means comprises means for measuring said elevation of said surface directly behind said at least one contact point at an angle, and means for compensating said measured elevation for the angle of measurement.

16. An apparatus for measuring the load bearing capacity of a traffic-carrying surface, comprising:

a weight supported on at least two surface-contacting wheels mutually spaced on at least one substantially horizontal axle for continuously proceeding along said surface;

first rack means mounted in front of said wheels transversely to the direction of travel of said weight second rack means mounted behind said wheels transversely to the direction of travel of said weight;

a first plurality of contactless distance measuring means mounted on said first rack means for measuring the elevation of said surface at a plurality of points directly in front and laterally of said wheels;

a second plurality of contactless distance measuring means mounted on said second rack means for measuring the elevation of said surface at a plurality of points directly behind and laterally of said wheels corresponding to said plurality of points directly in front and laterally of said wheels; and means for determining the difference between the corresponding surface elevation values measured by said first and second plurality of contactless distance measuring means.

* * * * *

UNITED STATES PATENT AND TRADEMARK OFFICE
CERTIFICATE OF CORRECTION

PATENT NO. : 4,781,058

DATED : November 1, 1988

INVENTOR(S) : Peter W. Arnberg

It is certified that error appears in the above-identified patent and that said Letters Patent is hereby corrected as shown below:

On the cover page under the heading "OTHER PUBLICATIONS", on line 1 please delete "tavarprofil" and substitute therefor --tvarprofil--.

On the cover page under the heading "OTHER PUBLICATIONS", on line 11 please delete "Highgways" and substitute therefor --Highways--.

In column 1, line 19, please delete "the" and substitute therefor --they--.

In column 1, line 30, please delete "traffic carrying" and substitute therefor --traffic-carrying--.

In column 1, line 35, please delete "traffic carrying" and substitute therefor --traffic-carrying--.

In column 2, line 7, please delete "angularlyshaped" and substitute therefor --angularly-shaped--.

In column 2, line 40, please delete "Beareernemalinger" and substitute therefor --beareernemalinger--.

UNITED STATES PATENT AND TRADEMARK OFFICE
CERTIFICATE OF CORRECTION

PATENT NO. : 4,781,058

DATED : November 1, 1988

INVENTOR(S) : Peter W. Arnberg

It is certified that error appears in the above-identified patent and that said Letters Patent is hereby corrected as shown below:

In column 2, lines 40 and 41, please delete "Forskelligt Inventeringsudestyr" and substitute therefor --forskelligt inventeringsudestyr--.

In column 3, line 28, after "schematic" please delete --:--

In column 3, line 43, after "invention;" please delete --and--.

In column 3, line 46, after "transducers" please insert --comprising another presently preferred--.

In column 3, line 46, after "invention" please delete "." and substitute therefor --;--.

In column 5, line 9, please delete "37" and substitute therefor --"--.

In column 5, line 29, please delete "is" and substitute therefor --as--.

UNITED STATES PATENT AND TRADEMARK OFFICE
CERTIFICATE OF CORRECTION

PATENT NO. : 4,781,058
DATED : November 1, 1988
INVENTOR(S) : Peter W. Arnberg

It is certified that error appears in the above-identified patent and that said Letters Patent is hereby corrected as shown below:

In column 5, line 34, after "transducer" please delete "-" and substitute therefor --18r--.

In column 6, line 7, after "velocity" please insert --of the--.

In column 6, line 16, after "computer" please insert --,--.

In column 6, line 16, after "example" please insert --,--.

In column 6, line 46, please delete "frequenoy" and substitute therefor --frequency--.

In column 7, line 59, please delete "e.g." and substitute therefor --<u>e.g.</u>--.

In column 8, line 66, please delete "apparent-to" and substitute therefor --apparent to--.

IN THE CLAIMS

In column 10, line 10, after "surface" please insert --at--.

In column 10, line 24, please delete "Surface" and substitute therefor --surface--.

UNITED STATES PATENT AND TRADEMARK OFFICE
CERTIFICATE OF CORRECTION

PATENT NO. : 4,781,058
DATED : November 1, 1988
INVENTOR(S) : Peter W. Arnberg

It is certified that error appears in the above-identified patent and that said Letters Patent is hereby corrected as shown below:

In column 10, line 44, please delete "last" and substitute therefor --least--.

In column 11, line 7, after "weight" please insert --;--.

Signed and Sealed this

Eighteenth Day of February, 1992

Attest:

HARRY F. MANBECK, JR.

*Attesting Officer*    *Commissioner of Patents and Trademarks*